US009248110B2

(12) United States Patent
Lehrer

(10) Patent No.: US 9,248,110 B2
(45) Date of Patent: Feb. 2, 2016

(54) COMPOSITIONS AND METHODS OF TREATING AND PREVENTING LUNG CANCER AND LYMPHANGIOLEIOMYOMATOSIS

(76) Inventor: Steven Lehrer, New York, NY (US)

(*) Notice: Subject to any disclaimer, the term of this patent is extended or adjusted under 35 U.S.C. 154(b) by 8 days.

(21) Appl. No.: 13/611,894

(22) Filed: Sep. 12, 2012

(65) Prior Publication Data
US 2013/0004436 A1 Jan. 3, 2013

Related U.S. Application Data

(63) Continuation-in-part of application No. PCT/US2011/028513, filed on Mar. 15, 2011.

(60) Provisional application No. 61/340,434, filed on Mar. 18, 2010, provisional application No. 61/397,533, filed on Jun. 14, 2010, provisional application No. 61/564,283, filed on Nov. 28, 2011.

(51) Int. Cl.
*A61P 11/00* (2006.01)
*A61K 31/155* (2006.01)
*A61K 38/20* (2006.01)
*A61K 38/21* (2006.01)

(52) U.S. Cl.
CPC ............... *A61K 31/155* (2013.01); *A61K 38/20* (2013.01); *A61K 38/21* (2013.01)

(58) Field of Classification Search
CPC .................................................... A61K 38/21
See application file for complete search history.

(56) References Cited

U.S. PATENT DOCUMENTS

| 7,229,614 | B2* | 6/2007 | Dabora et al. ............... 424/85.5 |
| 2002/0016287 | A1* | 2/2002 | Buckingham et al. .......... 514/3 |
| 2003/0059375 | A1* | 3/2003 | Perez-Soler et al. ........... 424/45 |
| 2006/0128792 | A1* | 6/2006 | Lee ............................... 514/453 |
| 2006/0172014 | A1* | 8/2006 | Curd et al. .................... 424/649 |
| 2008/0220078 | A1 | 9/2008 | Morton et al. |
| 2008/0299113 | A1 | 12/2008 | Arnold et al. |
| 2008/0312199 | A1 | 12/2008 | Glinsky |
| 2009/0208582 | A1 | 8/2009 | Johnston et al. |
| 2009/0209497 | A1* | 8/2009 | Folkman et al. .............. 514/154 |

FOREIGN PATENT DOCUMENTS

WO    WO 2008148074 A2 * 12/2008

OTHER PUBLICATIONS

Saito, "Chemical Genomics Identifies the Unfolded Protein Response as a Target for Selective Cancer Cell Killing during Glucose Deprivation", Cancer Res, 69(10):4225-34, 2009.*
Wang, "Overexpression of endoplasmic reticulum molecular chaperone GRP94 and GRP78 in human lung cancer tissues and its significance", Cancer Detection and Prevention 29, 544-551, 2005.*
Shaw, "LKB1 and AMPK control of mTOR signalling and growth", Acta Physil (Oxf), 196(1): 65-80, May 2009.*
Lee AS, GRP78 induction in cancer: therapeutic and prognostic implications. Cancer Res 2007; 67; 3496-3499.*
Fu Y, Lee AS. Glucose regulated proteins in cancer progression, drug resistance and immunotherapy. Cancer Biol Ther 2006;5;741-4.*
El-Hashemite, "Interferon-y-Jak-Stat Signaling in Pulmonary Lymphangioleiomyomatosis and Renal Angiomyolipoma", American Journal of Respiratory Cell and Molecular Biology, vol. 33, pp. 227-230, 2005.*
Tsakiridis, T., et al. "Metformin sensitizes human luncg cancer xenografts to ionizing radiation: Response of the AMPK pathway." Presentation Abstract No. 2491, AACR 102nd Annual Meeting, Orlando, FL. Apr. 4, 2010.
Algire, C., et al. "Metformin attenuates the stimulatory effect of a high-energy diet on in vivo LLC1 carcinoma growth." Endocr Relat Cancer. Sep. 2008;15(3):833-9. Epub May 9, 2008.
Antonoff, M.B., et al. "Teaching an old drug new tricks: metformin as a targeted therapy for lung cancer." Semin Thorac Cardiovasc Surg. 2010 Autumn;22(3):195-6.
Ben Sahra, I., et al. "Metformin in cancer therapy: a new perspective for an old antidiabetic drug?" Mol Cancer Ther. May 2010;9(5):1092-9. Epub May 4, 2010.
Chen, Y., et al. "Antidiabetic drug metformin (GlucophageR) increases biogenesis of Alzheimer's amyloid peptides via up-regulating BACE1 transcription." Proc Natl Acad Sci U S A. Mar. 10, 2009;106(10):3907-12. Epub Feb. 23, 2009.
Zarogoulidis, P., et al. "Feasibility and effectiveness of inhaled carboplatin in the treatment of NSCLC patients." 2010 ASCO Annual Meeting Abstracts.
Friedrich, M.J. "Researchers aim to stop tumor growth by shutting off cancer's fuel supply."JAMA. Mar. 17, 2010;303(11):1021-2.
Govindarajan, R., et al. "Thiazolidinediones and the risk of lung, prostate, and colon cancer in patients with diabetes." J Clin Oncol. Apr. 20, 2007;25(12):1476-81.
Johnson, I.S., et al. "Antitumor activity of glucagon." Cancer Res. Jun. 1959;19(5):557-60.
Landman, G.W., et al. "Metformin associated with lower cancer mortality in type 2 diabetes: ZODIAC-16." Diabetes Care. Feb. 2010;33(2):322-6. Epub Nov. 16, 2009.
Lee, W., et al. "Limited resection for non-small cell lung cancer: observed local control with implantation of I-125 brachytherapy seeds." Ann Thorac Surg. Jan. 2003;75(1):237-42; discussion 242-3.
Libby, G. et al. "New users of metformin are at low risk of incident cancer: a cohort study among people with type 2 diabetes." Diabetes Care. Sep. 2009;32(9):1620-5. Epub Jun. 29, 2009.
Lin, C., et al. "Metformin inhibits lung cancer cell growth and angiogenesis in vitra and in vivo Effect on IL6-Stat3 pathway." Presentation Abstract No. 71, AACR 101st Annual Meeting, Washington, D.C. Apr. 18, 2010.
Memmott, R.N., et al. "Metformin, an antidiabetic drug that modulates the AMPK/mTOR pathway, prevents tobacco carcinogen-induced lung tumorigenesis" [ABSTRACT]. In: Proceedings of the 101st Annual Meeting of the American Association for Cancer Research; Apr. 17-21, 2010; Washington, DC. Philadelphia (PA): AACR; 2010. Abstract nr 2928.

(Continued)

Primary Examiner — Robert T Crow
Assistant Examiner — John P Nguyen
(74) Attorney, Agent, or Firm — Robert C. Netter; Dann, Dorfman, Herrell and Skillman

(57) ABSTRACT

Compositions and methods for treating and preventing cancer, particularly lung cancer, lymphangioleiomyomatosis and asthma are provided.

23 Claims, No Drawings

(56) References Cited

OTHER PUBLICATIONS

Kim, K.W.., et al. "Activation of AMP-activated protein kinase (AMPK) enhances Radiosensitization via inhibition of mTOR pathway in Rapamycin=resistant non-small cell lung cancer cells." Presentation Abstract No. 2869, AACR 102nd Annual Meeting, Orlando, FL. Apr. 4, 2010.

Monami, M., et al. "Sulphonylureas and cancer: a case-control study." Acta Diabetol. Dec. 2009;46(4):279-84. Epub Dec. 10, 2008.

Onn, A., et al. "Development of an orthotopic model to study the biology and therapy of primary human lung cancer in nude mice." Clin Cancer Res. Nov. 15, 2003;9(15):5532-9.

Otterson, G.A., et al. "Phase I/II study of inhaled doxorubicin combined with platinum-based therapy for advanced non-small cell lung cancer." Clin Cancer Res. Apr. 15, 2010;16(8):2466-73. Epub Apr. 6, 2010.

Wauthoz, N., et al. "In vivo assessment of temozolomide local delivery for lung cancer inhalation therapy." Eur J Pharm Sci. Mar. 18, 2010;39(5):402-11. Epub Jan. 25, 2010.

Wolff, R.K., et al. "Toxicologic testing of inhaled pharmaceutical aerosols." Crit Rev Toxicol. 1993;23(4):343-69.

Yi, D., et al. "Inhalation Adjuvant Therapy for Lung Cancer." J Aero Med & Pulmon Drug Deliv. 2010;23:1-6.

Gagnadoux, F., et al. "Aerosol delivery of chemotherapy in an orthotopic model of lung cancer." Eur Respir J. Oct. 2005;26(4):657-61.

Riley, T., et al. "The benefits and challenges of PEGylating small molecules." Pharmaceutical Technology. Jul. 2008;32(7):88-94.

Luft, D., et al. "Lactic Acidosis in Biguanide-Treated Diabetics." Diabetologia. 1978;14:75-87.

Bolzano, K. "Biguanides: reasons for withdrawal of drugs and remaining indications." Acta Med Austriaca. 1978;5(3):85-88. [ABSTRACT].

* cited by examiner

COMPOSITIONS AND METHODS OF TREATING AND PREVENTING LUNG CANCER AND LYMPHANGIOLEIOMYOMATOSIS

This application is a continuation-in-part of PCT/US2011/028513, filed on Mar. 11, 2011, which claims priority to U.S. Provisional Application 61/340,434, filed Mar. 18, 2010, and U.S. Provisional Application 61/397,533, filed Jun. 14, 2010. This application also claims priority under 35 U.S.C. §119(e) to U.S. Provisional Patent Application No. 61/564,283, filed on Nov. 28, 2011. The entire disclosure of each of these applications is incorporated by reference herein.

FIELD OF THE INVENTION

The present invention relates to the field of oncology. Specifically, compositions and methods for treating, inhibiting, and/or preventing lung cancer are disclosed.

BACKGROUND OF THE INVENTION

Several publications and patent documents are cited throughout the specification in order to describe the state of the art to which this invention pertains. Each of these citations is incorporated herein by reference as though set forth in full.

Cancer cells and normal cells are metabolically different. Ninety years ago Otto Warburg found that while normal adult cells rely on mitochondrial oxidative phosphorylation to generate energy, cancer cells revert to a more primitive method of metabolizing glucose, aerobic glycolysis, fermenting glucose into lactate even in the presence of enough oxygen to support oxidative phosphorylation. Warburg proposed that this phenomenon (now called the Warburg effect) is an early step on the road to tumorigenesis. The Warburg effect has been demonstrated to occur across a wide spectrum of tumors and is found in about 70% of cases. It is generally accepted as a metabolic hallmark of cancer and is exploited by clinicians for the detection of tumors by 18-fluorodeoxyglucose positron emission tomography.

Lung tumors are already treated locally to achieve local control. $^{125}$I seed implantation along the resected margin for patients undergoing limited resection of lung cancer results in a relatively low incidence of local recurrence and may prolong survival (Lee et al. (2003) The Annals of Thoracic Surgery 75:237).

Aerosol formulations of anti-diabetic agents have been proposed to treat diabetes or a diabetes related condition susceptible of treatment by inhalation (U.S. Pat. No. 6,645,468). However, many drugs that are administered orally can be toxic to the lung when inhaled (Wolff et al. (1993) Crit. Rev. Toxicol., 23:343-369).

SUMMARY OF THE INVENTION

In accordance with one aspect of the instant invention, methods of treating, inhibiting (e.g., slowing or reducing), preventing, and/or inhibiting the onset of cancer, lymphangioleiomyomatosis, asthma, or chronic obstructive pulmonary disease in a subject are provided. In a particular embodiment, the method comprises administering a composition comprising at least one anti-diabetic agent and, optionally, at least one pharmaceutically acceptable carrier to the lungs of the subject, particularly by inhalation. In a particular embodiment, the method comprises administering at least buformin to a subject. The method may further comprise at least one other anti-cancer therapy such as the administration of at least one additional chemotherapeutic agent to the subject, administering radiation therapy to the subject, and/or resecting a lung tumor in the patient.

In accordance with another aspect of the instant invention, compositions for treating, inhibiting (e.g., slowing or reducing), preventing, and/or inhibiting the onset of cancer, lymphangioleiomyomatosis, asthma, or chronic obstructive pulmonary disease in a subject are provided. Inhalers comprising the composition are also provided.

DETAILED DESCRIPTION OF THE INVENTION

Drugs that are used in treating type 2 diabetes may be used to disrupt the above-described Warburg effect (see, e.g., Friedrich, M. J. (2010) JAMA, 303:1021-1022). Several studies have since shown that the widely used oral diabetes drug metformin may help in preventing cancer in diabetic patients (Libby et al. (2009) Diabetes Care 32:1620-1625; Monami et al. (2009) Acta Diabetol., 46:279-284; Landman et al. (2010) Diabetes Care 33:322-326). For example, Landman et al. show that patients with type 2 diabetes are at increased risk for cancer mortality. However, metformin use is associated with lower cancer mortality compared with those that did not use metformin. Algire et al. (Endocr. Relat. Cancer (2008) 15:833-839) has also shown that mice injected with Lewis lung LLC1 cells showed reduce tumor growth when orally administered metformin and fed a high-energy diet. However, orally administered metformin had no effect on tumor growth in the mice on a control diet. Notably, long-term treatment with metformin is associated with few adverse effects (Bolen et al. (2007) Ann. Intern. Med., 147:386-399).

The present invention provides pharmaceutical compositions and methods for the treatment, inhibition, and/or prevention of lung cancer or metastases to the lung. In a particular embodiment, the compositions comprise a therapeutically effective amount of at least one anti-diabetic agent and, optionally, at least one pharmaceutically acceptable carrier. The compositions may further comprise at least one additional chemotherapeutic agent. In a particular embodiment, the anti-diabetic agent is a biguanide or a glitazone. In another embodiment, the composition comprises at least one biguanide and at least one glitazone. Biguanides include, without limitation, metformin, phenformin, buformin, benfosformin, etoformin, tiformin, proguanil, and pharmaceutically acceptable salts or esters thereof. In a particular embodiment, the biguanide is buformin. Glitazones (also known as thiazolidinediones (TZDs)) include, without limitation, rosiglitazone (Avandia®), pioglitazone (Actos®), troglitazone (Rezulin®), and pharmaceutically acceptable salts or esters thereof. In a particular embodiment, the anti-diabetic agent is a sulphonylurea drug (e.g., acetohexamide, chlorpropamide, tolbutamide, glipizide, glyburide), a sulfonamide (e.g., tolazemide), an alpha-adrenergic antagonist (e.g., phentolamine), or pharmaceutically acceptable salts or esters thereof.

The present invention encompasses methods for treating, inhibiting, preventing, and/or inhibiting the onset of cancer, particularly lung cancer. The methods of the instant invention comprise the administration of at least one composition of the instant invention to a subject (e.g., mammal or human, including non-diabetic subjects). In a particular embodiment, the method comprises administering at least two anti-diabetic compounds to a subject (either in the same composition or separately), particularly at least one biguanide and at least one glitazone. In a particular embodiment, the compositions of the instant invention are administered by inhalation or orally, particularly by inhalation.

In a particular embodiment, the methods of the instant invention are used as an adjuvant therapy. The methods of the instant invention may further comprise the administration of at least one chemotherapeutic agent (prior, after, and/or simultaneous) to the subject. In a particular embodiment, the methods of the instant invention further comprise the administration of radiation therapy (e.g., ionizing radiation; prior, after, and/or simultaneous) to the subject. Indeed, it has since been show that metformin sensitizes human lung cancer cells to ionizing radiation (see, e.g., Tsakiridis et al. Abstract 2491, 102nd Meeting American Association for Cancer Research, 2011; Kim et al. Abstract 2869, 102nd Meeting American Association for Cancer Research, 2011). In still another embodiment, the methods comprise administering the composition(s) of the instant invention in conjunction (prior, after, and/or simultaneous) with cancer/tumor surgery (e.g., resection).

The present invention also encompasses methods of preparing a medicinal aerosol formulation. In a particular embodiment, the method comprises combining at least one medicament in an amount sufficient to provide a plurality of therapeutically effective doses and at least one fluid carrier in an amount sufficient to propel a plurality of said therapeutically effective doses from an aerosol canister. The method may further comprise dispersing the product. In a particular embodiment, the method further comprises combining a stabilizer in an effective stabilizing amount. In a particular embodiment, the method further comprises combining a cosolvent (e.g., ethanol).

Lung cancer cell growth in vivo and in vitro has since shown to be inhibited by metformin (Lin et al., "Metformin inhibits lung cancer cell growth and angiogenesis in vitro and in vivo: Effect on IL6-Stat3 pathway." Proc. 101st Annual Meeting of the Amer. Assoc. for Cancer Res.; 2010 Apr. 17-21; Washington, D.C. 51:19). As stated hereinabove, metformin may also be used for chemoprevention of lung cancer, particularly in high risk individuals (e.g., tobacco users, e.g., smokers, particularly heavy smokers). Indeed, metformin has since been shown to modulate the AMPK/mTOR pathway and prevents tobacco carcinogen-induced lung tumorigenesis in mice (Memmott et al., "Metformin, an antidiabetic drug that modulates the AMPK/mTOR pathway, prevents tobacco carcinogen-induced lung tumorigenesis", Proc. 101st Annual Meeting of the Amer. Assoc. for Cancer Res., 2010 Apr. 17-21, 51:#2928; Memmott et al. (2010) Cancer Prey. Res., 3:1066-1076; Antonoff et al. (2010) Semin Thoracic Surg., 22:195-196). mTOR is short for the mammalian target of rapamycin. Indeed, rapamycin (sirolimus) inhibits the growth and metastasis of cancer cells and is currently being tested in cancer treatment. However, because of its lung toxicity, rapamycin would not be safe to deliver to the lung as an inhaled preparation.

Administration

Delivery of drugs to the lung by way of inhalation is an important means of treating a variety of conditions, including such common local conditions as cystic fibrosis, pneumonia, bronchial asthma and chronic obstructive pulmonary disease, some systemic conditions, including hormone replacement, pain management, immune deficiency, erythropoiesis, diabetes, lung cancer, etc. Yi et al. (J. Aerosol Med. Pulm. Drug Deliv. (2010) 23:181-7) review the literature pertaining to lung cancer adjuvant therapy and inhalation lung cancer chemoprevention. Yi et al. state that inhalation of chemotherapy as an adjuvant in Stage II non small-cell lung cancer (NSCC) and inhalation of chemopreventive agents in Stage I adenocarcinomas are direct paths to improve lung cancer therapy as well as demonstrate the utility of inhalation therapy.

Normal lung tissue is protected by cilia, which beat constantly to move a protective layer of fluid and mucous. Lung tumors have few or no cilia, little covering of fluid, and so are vulnerable to inhaled chemotherapy. Inhaled cisplatin, inhaled carboplatin, inhaled taxanes, and inhaled anthracyclines may be used for lung cancer treatment (Landman et al. (2010) Diabetes Care, 33:322-326; U.S. Pat. Nos. 6,419,900; 6,419,901; 6,451,784; 6,793,912; U.S. Patent Application Publication No. 2003/0059375; U.S. Patent Application Publication No. 2004/0039047; Zarogoulidis et al. (2010). J. Clin. Oncol., 28:e17511). Inhaled doxorubicin, inhaled liposomes, and inhaled temozolomide may be used to treat lung metastases (Otterson et al. (2010) Clin. Cancer Res., 16:2466-2473; Wauthoz et al. (2010) Eur. J. Pharm. Sci., 39:402-411; U.S. Pat. No. 7,288,243; U.S. Patent Application Publication No. 2008/0008662).

Anti-diabetic drugs, e.g. insulin and metformin, are among the drugs that are administered to the lung for diabetes treatment (U.S. Pat. No. 6,447,750). Such drugs are commonly administered to the lung in the form of an aerosol of particles of respirable size (less than about 10 μm in diameter). The aerosol formulation can be presented as a liquid or a dry powder (U.S. Pat. No. 6,540,983). In order to assure proper particle size in a liquid aerosol, particles can be prepared in respirable size and then incorporated into a colloidal dispersion either containing a propellant as a metered dose inhaler (MDI) or air, such as in the case of a dry powder inhaler (DPI). Alternatively, formulations can be prepared in solution form in order to avoid the concern for proper particle size in the formulation. Solution formulations must nevertheless be dispensed in a manner that produces particles or droplets of respirable size. Insulin and glucagon might be included in the present invention, since they can inhibit tumor growth (Johnson et al. (1959) Cancer Res., 19:557-560).

Bugelski et al. teach the use of inhaled CXCL13 antagonists for the treatment of inflammatory diseases (U.S. Patent Application Publication No. 2008/0014201). For administration by inhalation, the compounds are delivered in the form of aerosolized particles from a pressurized container or dispenser that contains a suitable propellant, e.g., a gas such as carbon dioxide, or a nebulizer. Alternatively, compositions formulated as particles can be dispersed by electrostatic, mechanical means including vibrations, or ultrasonic means as taught in U.S. Pat. Nos. 4,530,464; 4,533,082; 5,838,350; 6,113,001; 6,514,496; 5,518,179; 5,152,456; 5,261,601; and 4,605,167. Pulmonary drug delivery formulations are also provided in Pilcer et al. (Intl. J. Pharm. (2010) 392:1-19).

The above-referenced methods of administering a drug to the lungs may be used for administering the instant compositions to the lungs of a subject.

For metered dose inhaler application, an aerosol formulation is filled into an aerosol canister equipped with a metered dose valve. In the hands of the patient the formulation is dispensed via an actuator adapted to direct the dose from the valve to the patient. In a particular embodiment, the instant invention provides a metered dose inhaler containing a medicinal aerosol formulation/composition, wherein the composition comprises at least one anti-diabetic agent in particulate form in a therapeutically effective amount and at least one pharmaceutically acceptable carrier such as a fluid carrier and a stabilizer comprising a water addition which is present in an amount which (1) is in excess of nascent formulation water and (2) is present in an amount to stabilize the formulation to prevent settling, creaming or flocculation for a time sufficient to allow reproducible dosing of the drug after agitation of the formulation. The stabilizer may be present in excess in an amount of about 10 part by weight to about 5000 parts by weight based on one million parts by total weight of the medicinal aerosol formulation. In a particular embodiment, the anti-diabetic agent is metformin. The fluid carrier may be a propellant, e.g., 1,1,1,2-tetrafluoroethane, 1,1,1,2,3,3,3-heptafluoropropane or a mixture thereof. In another embodiment, the fluid carrier is a hydrocarbon (e.g., n-butane, propane, isopentane, or a mixture thereof). The composition may further comprise a co-solvent (e.g., ethanol).

According to one aspect, the instant invention encompasses a medicinal aerosol formulation, and more particularly a medicinal aerosol formulation, comprising at least one anti-diabetic agent to treat lung cancer (inclusive of malignant tumor metastatic to the lungs). In a particular embodiment, a stable aerosol formulation for the treatment of lung cancer and conditions related thereto is provided.

Epidemiological studies show a decrease in cancer incidence in metformin-treated patients. Metformin decreases insulin resistance and indirectly reduces insulin level, a beneficial effect because insulin promotes cancer cell growth. Several reports outline a direct inhibitory effect of metformin on cancer cell growth and an antitumoral action. Finally, metformin activates the AMP activated protein kinase (AMPK) pathway, a major sensor of the energetic status of the cell, which is a promising therapeutic target in cancer (Ben Sahra et al. (2010) Molecular Cancer Therapeutics 9:1092-1099). Oral thiazolidinedione use was also associated with a 33% reduction in the risk of lung cancer (Govindarajan et al. (2007) J. Clin. Oncol., 25:1476).

In a particular embodiment, the biguanide buformin is administered to the lungs of the subject. Typical inhaled asthma medications are about 10-100 µg per day, inhaled insulin requires 1-10 mg per day, and inhaled antibiotics are 60-150 mg day. Metformin is generally taken orally twice daily with a maximum total dose of 2.5 g/day. Ideally, one can drop the inhaled dose of an oral drug by a factor of 10-20 to get the same local concentration in the lung as by oral administration. Accordingly, in order to equal the oral dose of metformin, one would have to inhale 125-250 mgs day. Even if this is delivered in 3 doses a day, it would be 40-80 mgs/dose. The best inhalation delivery systems at this payload get ~50% of the packaged dose into the lungs. Accordingly, a capsule based powder inhalation system would likely have to be used. Delivering this much metformin powder to the lung is at the upper limit of acceptability and might result in coughing and reduced compliance.

In contrast, buformin has about eight times the potency of metformin. The usual maximum oral dose of buformin is 300 mg per day. Dropping the inhaled dose by a factor of 10 to 20, three doses per day inhaled buformin could be given at about 5 mg to 10 mg per dose, much less than metformin. At this dosage there would be no coughing or bronchospasm at all and compliance would be excellent. Furthermore, this smaller dose of buformin, about 15 mg to 30 mg per day, would not produce lactic acid acidosis, the main biguanide complication (Bolzano, K. (1978) Acta Med Austriaca. 5:85-8). The toxic oral buformin dose was determined to be 329±30 mg/day in 24 patients who developed lactic acidosis on buformin whereas another group of 24 patients on 258±25 mg/day buformin did not develop lactic acidosis (Luft et al. (1978) Diabteologia 14:75). Notably, lactic acid acidosis is a condition with a 50% mortality rate. Accordingly, it is important to keep buformin levels below toxic levels. Surprisingly, the delivery of inhaled buformin allows for the administration of safe levels of buformin while still providing an effective therapeutic strategy against lung cancer. In a particular embodiment of the instant invention, about 1 mg to about 100 mg, about 5 mg to about 50 mg, about 10 mg to about 40, or, more particularly, about 15 mg to about 30 mg of buformin is administered per day.

In addition to the above, buformin has a long lung residence time. Buformin has an octanol/water partition coefficient (log P) of −1.2 and is hydrophilic. Hydrophilic small molecules with a log P less than 0 have a mean lung half life ($t\frac{1}{2}$) of about one hour. The long lung residence time of buformin could be increased even further with an appropriate formulation.

The aerosol pharmaceutical formulations for use in combination therapies of the present invention may include, as optional ingredients, pharmaceutically acceptable carriers, diluents, solubilizing or emulsifying agents, and salts of the type that are well-known in the art. Examples of such substances include normal saline solutions, such as physiologically buffered saline solutions, and water.

In a particular embodiment of the instant invention, the therapeutic agents may be delivered via an inhaler that produces an aerosol mimicking the distribution of cigarette and cigar smoke in the lung (e.g., an electronic cigarette).

The route of administration of anti-diabetic drugs or disease suppressive fragments or analogs thereof according to the present invention may be in an aerosol or inhaled form (U.S. Pat. No. 6,878,749). The anti-diabetic drugs and related compounds of the present invention can be administered as a dry powder or in an aqueous solution. Aerosol pharmaceutical formulations may comprise for example, a physiologically-acceptable buffered saline solution containing between about 1 mg and about 1000 mg of anti-diabetic drugs, disease suppressive fragments or analogs thereof.

Dry aerosol in the form of finely divided solid particles of anti-diabetic drugs, disease suppressive fragments or analogs thereof that are not dissolved or suspended in a liquid are also useful in the practice of the present invention. The anti-diabetic drugs may be in the form of dusting powders and comprise finely divided particles having an average particle size of between about 1 and 5 microns, preferably between 2 and 3 microns. Finely divided particles may be prepared by pulverization and screen filtration using techniques well known in the art. The particles may be administered by inhaling a predetermined quantity of the finely divided material, which can be in the form of a powder.

Specific non-limiting examples of the carriers and/or diluents that are useful in the aerosol pharmaceutical formulations used for combination therapies of the present invention include water and physiologically-acceptable buffered saline solutions such as phosphate buffered saline solutions pH 7.0-8.0.

The aerosol pharmaceutical formulations of the present invention are already in wide use (e.g., U.S. Pat. No. 4,243,548). These formulations may be administered in the form of an aerosol spray using for example, a nebulizer such as those described in U.S. Pat. Nos. 4,624,251; 3,703,173; 3,561,444; and 4,635,627). The aerosol material is inhaled by the subject to be treated.

Other systems of aerosol delivery may be used, such as the pressurized metered dose inhaler (MDI) and the dry powder inhaler as disclosed in U.S. Pat. No. 4,534,343. Aerosol delivery systems of the type disclosed herein are available from numerous commercial sources including Fisons Corporation (Bedford, Mass.), Schering Corp. (Kenilworth, N.J.), American Pharmoseal Co., (Valencia, Calif.), and Activaero (Germany).

In addition, a controlled release pulmonary drug delivery system may be employed. For example, liposomal delivery technology could provide a sustained benefit of drug in the lung while minimizing systemic exposure.

In a particular embodiment, metformin is administered at about 150-200 mg/dose or buformin is administered at about 15-30 mg/dose, although more or less can be administered as stated hereinabove. This dosage limits coughing and the time necessary to deliver the drug. The above dosage yields very high local lung concentrations and may be supplemented with oral delivery. Notably, small molecules may have short residence times in the lungs. As such, dosing may be frequent to maintain adequate levels of drug at the tissue level.

The compositions of the instant invention may further comprise a propellant (e.g., a compressed gas such as compressed air, carbon dioxide, nitrogen, and/or an organic propellant such as fluorochlorohydrocarbon). In a particular embodiment, the propellant is 1,1,1,2-tetrafluoroethane, 1,1,1,2,3,3,3-heptafluoropropane, or a mixture thereof. The aerosol dosage forms can also take the form of a pump-atomizer.

The compositions of the instant invention may comprise a fluid carrier. In a particular embodiment, the fluid carrier is a hydrocarbon. Exemplary hydrocarbons include, without limitation, n-butane, propane, isopentane, and mixtures thereof.

The compositions of the instant invention may further comprise a stabilizer. The stabilizer may be water. The compositions may further comprise a cosolvent (e.g., a cosolvent comprising ethanol).

One skilled in the art appreciates that a pharmaceutical composition comprising an anti-diabetic agent can be administered to a subject by various routes including, for example, by inhalation, orally or parenterally, such as intravenously (i.v.), intramuscularly, subcutaneously, intraorbitally, intranasally, intracapsularly, intraperitoneally (i.p.), intracisternally, intra-tracheally (i.t), intra-articularly or by passive or facilitated absorption through the skin using, for example, a skin patch or transdermal iontophoresis, respectively. Thus, an anti-diabetic agent can be administered systemically by injection, intubation, or orally, or can be administered locally by topical application, the latter of which can be passive, for example, by direct application of an ointment or powder, or active, for example, and most preferably, using a nasal spray or inhalant.

Administration of an anti-diabetic agent by inhalation is a particularly preferred means of treating or preventing lung cancer. One skilled in the art would recognize that an anti-diabetic agent can be suspended or dissolved in an appropriate pharmaceutically acceptable carrier and administered, for example, directly into the lungs using a nasal spray or inhalant.

A pharmaceutical composition comprising an anti-diabetic agent can be administered as an aerosol formulation which contains the inhibitor in dissolved, suspended or emulsified form in a propellant or a mixture of solvent and propellant. The aerosolized formulation is then administered through the respiratory system or nasal passages.

An aerosol formulation used for nasal administration may be an aqueous solution designed to be administered to the nasal passages in drops or sprays. Nasal solutions are generally prepared to be similar to nasal secretions and are generally isotonic and slightly buffered to maintain a pH of about 5.5 to about 6.5, although pH values outside of this range can additionally be used (e.g., a pH of about 5 to about 8). Antimicrobial agents or preservatives can also be included in the formulation.

An aerosol formulation used for inhalations and inhalants may be designed so that the anti-diabetic agent is carried into the respiratory tree of the patient administered by the nasal or oral respiratory route. Inhalation solutions can be administered, for example, by a nebulizer. Inhalations or insufflations, comprising finely powdered or liquid drugs, are delivered to the respiratory system as a pharmaceutical aerosol of a solution or suspension of the drug in a propellant.

An aerosol formulation may contain a propellant to aid in disbursement of the anti-diabetic agent. Propellants can be liquefied gases, including halocarbons, for example, fluorocarbons such as fluorinated chlorinated hydrocarbons, hydrochlorofluorocarbons, and hydrochlorocarbons as well as hydrocarbons and hydrocarbon ethers (Remington's Pharmaceutical Sciences 18th ed., Gennaro, A. R., ed., Mack Publishing Company, Easton, Pa. (1990)). The propellant may be, e.g., 1,1,1,2-tetrafluoroethane, 1,1,1,2,3,3,3-heptafluoropropane or a mixture thereof.

Halocarbon propellants useful in the invention include fluorocarbon propellants in which all hydrogens are replaced with fluorine, hydrogen-containing fluorocarbon propellants, and hydrogen-containing chlorofluorocarbon propellants. Halocarbon propellants are described in, for example, U.S. Pat. Nos. 5,376,359 and 5,776,434.

Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as numerous other ethers.

The anti-diabetic agent can also be dispensed with a compressed gas. The compressed gas is generally an inert gas such as carbon dioxide, nitrous oxide or nitrogen.

An aerosol formulation of the invention can also contain more than one propellant. For example, the aerosol formulation can contain more than one propellant from the same class such as two or more fluorocarbons. An aerosol formulation can also contain more than one propellant from different classes. An aerosol formulation can contain any combination of two or more propellants from different classes, for example, a fluorohydrocarbon and a hydrocarbon.

Effective aerosol formulations can also include other components, for example, ethanol, isopropanol, propylene glycol, as well as surfactants or other components such as oils and detergents (see, e.g., Remington's Pharmaceutical Sciences, 1990; U.S. Pat. No. 5,776,434). These aerosol components can serve to stabilize the formulation and lubricate valve components.

The aerosol formulation can be packaged under pressure and can be formulated as an aerosol using solutions, suspensions, emulsions, powders and semisolid preparations. A solution aerosol may comprise a solution of an active ingredient such as an anti-diabetic agent in pure propellant or as a mixture of propellant and solvent. The solvent is used to dissolve the active ingredient and/or retard the evaporation of the propellant. Solvents useful in the invention include, for example, water, ethanol and glycols. A solution aerosol contains the active ingredient anti-diabetic agent and a propellant and can include any combination of solvents and preservatives or antioxidants.

An aerosol formulation can also be a dispersion or suspension. A suspension aerosol formulation may contain a suspension of an anti-diabetic agent and a dispersing agent. Dispersing agents useful in the invention include, for example, sorbitan trioleate, oleyl alcohol, oleic acid, lecithin and corn oil. A suspension aerosol formulation can also include lubricants and other aerosol components.

An aerosol formulation can similarly be formulated as an emulsion. An emulsion can include, for example, an alcohol such as ethanol, a surfactant, water and propellant, as well as the active ingredient anti-diabetic agent. The surfactant can be nonionic, anionic or cationic. One example of an emulsion can include, for example, ethanol, surfactant, water and propellant. Another example of an emulsion can include, for example, vegetable oil, glyceryl monostearate and propane.

An aerosol formulation containing an anti-diabetic agent may have a minimum of 90% of the particles in inhalation products, less than about 10 or 25 μm, more particularly between about 0.5 and about 10 μm, to maximize delivery and deposition of the an anti-diabetic agent to respiratory fluids. In particular, the particle size can be from about 1 to about 5 μm, more particularly about 3 to about 3 μm.

A pharmaceutical composition comprising an anti-diabetic agent also can be incorporated, if desired, into liposomes, microspheres, microbubbles, or other polymer matrices (see, e.g., Gregoriadis, Liposome Technology, Vols. I to III, 2nd ed., CRC Press, Boca Raton Fla. (1993)). Liposomes, for example, which consist of phospholipids or other lipids, are nontoxic, physiologically acceptable and metabolizable carriers that are relatively simple to make and administer. Liposome-based methods are useful since in certain circumstances peptides can be damaged (i.e., structural damage) during preparation with carriers. Thus, for certain applications of particular aspects of the instant invention, it may be preferable to utilize liposome-based delivery. For example, suitable methods are described in Torchilin (Advanced Drug Delivery Reviews (2008) 60:548-558); Cryan et al. (Advanced Drug Delivery Reviews (2007) 59:1133-1151); Kleemann et al. (J. Controlled Release (2005) 109:299-316; and Cryan et al. (Molecular Pharmaceutics (2006) 3:104-112).

Nanoparticles can also be used to deliver the anti-diabetic agent, particularly to the pulmonary system. As one of skill in the art will appreciate, a nanoparticle in accordance with the methods and compositions of the present invention can be composed of a variety of injectable biodegradable polymers. Nanoparticles are said to be biodegradable if the polymer of the nanoparticle dissolves or degrades within a period that is acceptable in the desired application (usually in vivo therapy), usually less than five years, and desirably less than one year, upon exposure to a physiological solution of pH 6-8 having a temperature of between 25° C. and 37° C. As such, a nanoparticle for use in accordance with the methods and compositions of the present invention can be composed of homopolymers or copolymers prepared from monomers of polymers, wherein the copolymer can be of diblock, triblock, or multiblock structure as described in U.S. Patent Application Publication No. 2006/0067925. Suitable polymers include, but are not limited to, poly(lactide-co-glycolides), poly(lactic acid), poly(alkylene glycol), polybutylcyanoacrylate, poly(methylmethacrylate-co-methacrylic acid), poly-allylamine, polyanhydride, polyhydroxybutyric acid, or polyorthoesters and the like. Particular combinations and ratios of polymers are well-known to the skilled artisan and any suitable combination can be used in the nanoparticle formulations of the present invention. Suitable formulations for use with the inhibitory peptide described herein are disclosed in international application PCT/US08/069519, which is incorporated by reference. Generally, the resulting nanoparticle typically ranges in size from between 1 nm and 1000 nm, or more desirably between 1 nm and 100 nm.

To increase mean residence time in the lung, the therapeutic agent (e.g., a biguanide anti-diabetic) may be modified such as by pegylation, lipidation, acylation, glycosylation, and the like. In a particular embodiment, the therapeutic agent is pegylated. PEGylating small molecules enhances and optimizes drug delivery. More specifically, PEGylation causes greater efficacy, reduces side effects, reduces the dosing schedule, and increases patient compliance (Riley et al. (2008) Pharm. Tech., 32:88-94).

In order to treat or prevent lung cancer, an anti-diabetic agent may be administered in an effective dose. The total treatment dose can be administered to a subject as a single dose or can be administered using a fractionated treatment protocol, in which multiple doses are administered over a more prolonged period of time, for example, over the period of a day to allow administration of a daily dosage or over a longer period of time to administer a dose over a desired period of time. One skilled in the art would know that the amount of an anti-diabetic agent required to obtain an effective dose in a subject depends on many factors, including the particular cancer being treated, the age, weight and general health of the subject, as well as the route of administration and the number of treatments to be administered. In view of these factors, the skilled artisan would adjust the particular dose so as to obtain an effective dose for treating an individual having lung cancer.

The effective dose of an anti-diabetic agent will depend on the mode of administration, and the weight of the individual being treated. The dosages described herein are generally those for an average adult. The dose will generally range from about 1 mg to about 500 mg/dose, more particularly about 10 mg to about 300 mg/dose, more particularly about 100 mg to about 250 mg/dose.

When administering high doses of an anti-diabetic agent, one skilled in the art can monitor for any possible adverse side effects. Methods of monitoring adverse side effects of an anti-diabetic agent are known in the art. One of skilled in the art can monitor for any adverse side effects and, if necessary, adjust the dosage to minimize adverse side effects while optimizing the effectiveness of treating or preventing lung cancer.

The concentration of an anti-diabetic agent in a particular formulation will depend on the mode and frequency of administration. A given daily dosage can be administered in a single dose or in multiple doses so long as the anti-diabetic agent concentration in the formulation results in the desired daily dosage. One skilled in the art can adjust the amount of an anti-diabetic agent in the formulation to allow administration of a single dose or in multiple doses that provide the desired concentration of an anti-diabetic agent over a given period of time.

As explained hereinabove, in an individual suffering from lung cancer (particularly a more severe/aggressive form of the disease), administration of an anti-diabetic agent can be particularly useful when administered in combination, for example, with at least one other conventional anti-cancer therapy. The skilled artisan would administer an anti-diabetic agent, alone or in combination with a second agent/therapy, based on the clinical signs and symptoms exhibited by the individual and would monitor the effectiveness of such treatment using routine methods.

When an anti-diabetic agent is administered in combination with one or more other anti-cancer agent, the anti-diabetic agent and other anti-cancer agent can be co-administered in the same formulation. Alternatively, the anti-diabetic agent and other anti-cancer agent can be administered simultaneously in separate formulations. In addition, the anti-diabetic agent can be administered in separate formulations, where the separate formulations are not administered simultaneously but are administered during the same period of treatment, for example, during a daily or weekly period of treatment.

Administration of the pharmaceutical preparation is preferably in a "prophylactically effective amount" or a "therapeutically effective amount" (as the case may be, although prophylaxis may be considered therapy), this being sufficient to show benefit to the individual. This amount prevents, alleviates, abates, or otherwise reduces the severity of symptoms in a patient.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art. As mentioned previously, a preferred embodiment of the invention comprises aerosolized delivery of an anti-diabetic agent to the lungs of a patient in need thereof. The anti-diabetic agent described herein can be delivered orally or injected intra-peritoneally (i.p.), intravenously (i.v.), or intratracheally (i.t.). Formulation, dosages and treatment schedules have also been described hereinabove.

The compositions of the instant invention may also be used to treat pulmonary lymphangioleiomyomatosis. Pulmonary lymphangioleiomyomatosis (LAM) is a rare disease of young women, with an incidence of less than one case per 100,000 population per year. LAM is associated with smooth muscle cell infiltration and cystic destruction of the lung. Clinically, LAM is characterized by progressive dyspnea on exertion, recurrent pneumothorax, abdominal and thoracic lymphadenopathy, and abdominal tumors. Oral sirolimus (rapamycin) has recently been reported to be an effective therapy that halts progression of LAM (McCormack et al. (2011) New Eng. J. Med., 364:1595-606). Rapamycin works by inhibiting mTOR, the mammalian target of rapamycin, a serine/threonine protein kinase that regulates cell growth. Because LAM is predominantly a pulmonary disease, an inhaled therapy, targeting only the lung, would be highly desirable. Rapamycin (sirolimus) cannot be safely inhaled because of its well-documented lung toxicity, interstitial pneumonitis (Chhajed et al. (2006) 73:367-374). An inhaled version of a biguanide (e.g., buformin) can be used to treat LAM. Biguanides also inhibit mTOR, but have no known lung toxicity after decades of use in millions of patients. The inhaled therapy may be combined with parenteral interferon and/or interleukin.

The instant invention also encompasses methods of treating and/or inhibiting asthma (e.g., refractory asthma) and/or chronic obstructive pulmonary disease (COPD). The compositions of the instant invention may also be administered to a subject to treat asthma. Like bronchial thermoplasty (Cox et al. (2007) New Eng. J. Med., 356:1327-1337), the administration of the compositions of the instant invention can shrink smooth muscle and relieve asthma symptoms.

Definitions

The following definitions are provided to facilitate an understanding of the present invention:

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a solvent, a diluent, stabilizer, adjuvant, excipient, auxilliary agent, propellant, or vehicle with which an active agent of the present invention is administered. The carrier is typically selected based on it being appropriate for the desired route of administration of the pharmaceutical composition. Except insofar as any conventional media or agent is incompatible with the compounds to be administered, its use in the pharmaceutical preparation is contemplated. Examples of pharmaceutically acceptable carriers include, without limitation, sterile liquids, water, buffered saline, ethanol, polyol (for example, glycerol, propylene glycol, liquid polyethylene glycol and the like), dimethyl sulfoxide (DMSO), oils, detergents, suspending agents, carbohydrates (e.g., glucose, sucrose or dextran), antioxidants (e.g., ascorbic acid or glutathione), chelating agents, low molecular weight proteins, or suitable mixtures thereof. Suitable pharmaceutical carriers are described in, e.g., "Remington's Pharmaceutical Sciences" (Ed. Gennaro; Mack Publishing, Easton, Pa.) and "Remington: The Science and Practice of Pharmacy" (Ed. Troy; Lippincott Williams & Wilkins, Baltimore, Md.).

Chemotherapeutic agents are compounds that exhibit anti-cancer activity and/or are detrimental to a cell (e.g., a toxin). Suitable chemotherapeutic agents include, but are not limited to: toxins (e.g., saporin, ricin, abrin, ethidium bromide, diptheria toxin, and Pseudomonas exotoxin); taxanes; alkylating agents (e.g., temozolomide, nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes (e.g., cisplatin, carboplatin, tetraplatin, ormaplatin, thioplatin, satraplatin, nedaplatin, oxaliplatin, heptaplatin, iproplatin, transplatin, and lobaplatin); bioreductive alkylators such as mitomycin, procarbazine, dacarbazine and altretamine); DNA strand-breakage agents (e.g., bleomycin); topoisomerase II inhibitors (e.g., amsacrine, menogaril, amonafide, dactinomycin, daunorubicin, N,N-dibenzyl daunomycin, ellipticine, daunomycin, pyrazoloacridine, idarubicin, mitoxantrone, m-AMSA, bisantrene, doxorubicin (adriamycin), deoxydoxorubicin, etoposide (VP-16), etoposide phosphate, oxanthrazole, rubidazone, epirubicin, bleomycin, and teniposide); DNA minor groove binding agents (e.g., plicamydin); antimetabolites (e.g., folate antagonists such as methotrexate and trimetrexate); pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); anthracyclines; and tubulin interactive agents (e.g., vincristine, vinblastine, and paclitaxel (Taxol®)).

Radiation therapy refers to the use of high-energy radiation from x-rays, gamma rays, neutrons, protons and other sources to target cancer cells. Radiation may be administered externally or it may be administered using radioactive material given internally. Chemoradiation therapy combines chemotherapy and radiation therapy.

As used herein, the term "anti-diabetic agent" refers an agent that prevents or alleviates the symptoms of diabetes. The term "anti-diabetic agent" includes compounds that improve/treat insulin resistance and/or decrease plasma glucose levels in patients with diabetes. Anti-diabetic agents include, without limitation: 1) PPARγ agonists (e.g., pioglitazone, rosiglitazone, etc.); 2) biguanides (e.g., metformin, etc.); 3) sulfonylureas (e.g., glibenclamide, glimepiride, glipizide, glyburide, etc.); 4) nonsulfonylureas (e.g., nateglinide, repaglimide, etc.); 5) PPARα/γ agonists (e.g., GW-2331, etc.); 6) DPP-IV-inhibitors (e.g., LAF-237, MK-0431, BMS-477118, GSK23A, etc.); 7) Glucokinase activators (see, e.g., WO 00/58293); and 8) α-Glucosidase inhibitors (e.g., acarbose, miglitol, etc.). The anti-diabetic agent may also be an mTOR inhibitor or an AMPK activator. In a particular embodiment, the mTor inhibitor inhibits mTORC1 preferentially over mTORC2, particularly where the mTor inhibitor has no significant inhibitory activity against mTORC2. Examples of mTOR inhibitors include, without limitation, CCI-779; rapamycin; AP23573; RAD001; and cell cycle inhibitor-779 (CCI-779). Examples of AMPK activators include, without limitation, leptin, adiponectin, metformin, and AICAR (5-aminoimidazole-4-carboxamide).

The following example provides illustrative methods of practicing the instant invention, and is not intended to limit the scope of the invention in any way.

EXAMPLE

Nude mice with implants of human lung tumors will be used to show the effect of metforminin on lung cancer. For example, Gagnadoux et al. (Eur. Respir. J. (2005) 26:657-661) describe the intrabronchial implantation of large cell carcinoma (NCI-H460) cells BALB/c nude mice. Onn et al. (Clin. Cancer Res. (2003) 9:5532-5539 also describe the injection of human lung adenocarcinoma (PC14PE6), bronchioloalveolar carcinoma (NCI-H358), squamous cell carcinoma (NCI-H226), poorly differentiated non-small cell lung cancer (NCI-H1299 and A549), and small cell lung cancer (NCI-H69) cells into the lungs of nude mice. The mice will be treated by spraying (e.g., with an Aerogen® inhaler (Galway, Ireland)) a liquid aerosol of a biguanide, such as buformin, multiple times daily into their lungs for a week and evaluating for evidence of tumor shrinkage.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of treating lung cancer or lymphangioleiomyomatosis in the lung in a subject in need thereof comprising administering a composition comprising at least one antidiabetic agent to the lungs of said subject, wherein said antidiabetic agent is buformin or a pharmaceutically acceptable salt or ester thereof.

2. The method of claim 1, wherein said subject is a human.

3. The method of claim 1, further comprising administering at least one chemotherapeutic agent to said subject.

4. The method of claim 1, further comprising administering radiation therapy to said subject.

5. The method of claim 1, further comprising resecting a lung tumor in said patient.

6. The method of claim 1, wherein said composition further comprises at least one pharmaceutically acceptable carrier.

7. The method of claim 1, wherein said composition is administered by inhalation.

8. The method of claim 7, wherein said composition comprises a propellant.

9. The method of claim 8, wherein said propellant is a halocarbon or a hydrocarbon.

10. The method of claim 9, wherein said hydrocarbon is selected from the group consisting of propane, isobutane, n-butane, pentane, isopentane, and neopentane.

11. The method of claim 8, wherein said propellant is a compressed gas.

12. The method of claim 11, wherein said compressed gas is air or an inert gas.

13. The method of claim 12, wherein said inert gas is selected from the group consisting of carbon dioxide, nitrous oxide, and nitrogen.

14. The method of claim 7, wherein said composition is administered by a metered dose inhaler.

15. The method of claim 6, wherein said pharmaceutically acceptable carrier comprises ethanol or water.

16. The method of claim 1, wherein said method comprises inhibiting lymphangioleimymatosis in the lung of a subject in need thereof.

17. The method of claim 7, wherein said composition is administered by a dry powder inhaler.

18. The method of claim 9, wherein said halocarbon is a fluorocarbon or a hydrogen-containing fluorocarbon.

19. The method of claim 16, further comprising the administration of interferon or interleukin for the treatment of lymphangioleiomyomatosis.

20. The method of claim 1, further comprising the administration of a glitazone.

21. The method of claim 1, wherein said method consists of administering a composition consisting of buformin or a pharmaceutically acceptable salt or ester thereof and a pharmaceutically acceptable carrier to the lungs of said subject.

22. The method of claim 1, wherein said method consists of administering a chemotherapeutic agent and a composition consisting of buformin or a pharmaceutically acceptable salt or ester thereof and a pharmaceutically acceptable carrier to the lungs of said subject.

23. The method of claim 1, wherein said method consists of administering a composition consisting of buformin or a pharmaceutically acceptable salt or ester thereof, a glitazone, and a pharmaceutically acceptable carrier to the lungs of said subject.

* * * * *